July 28, 1953 H. M. TIRET Plant Pat. 1,206
FUCHSIA PLANT
Filed Oct. 25, 1949
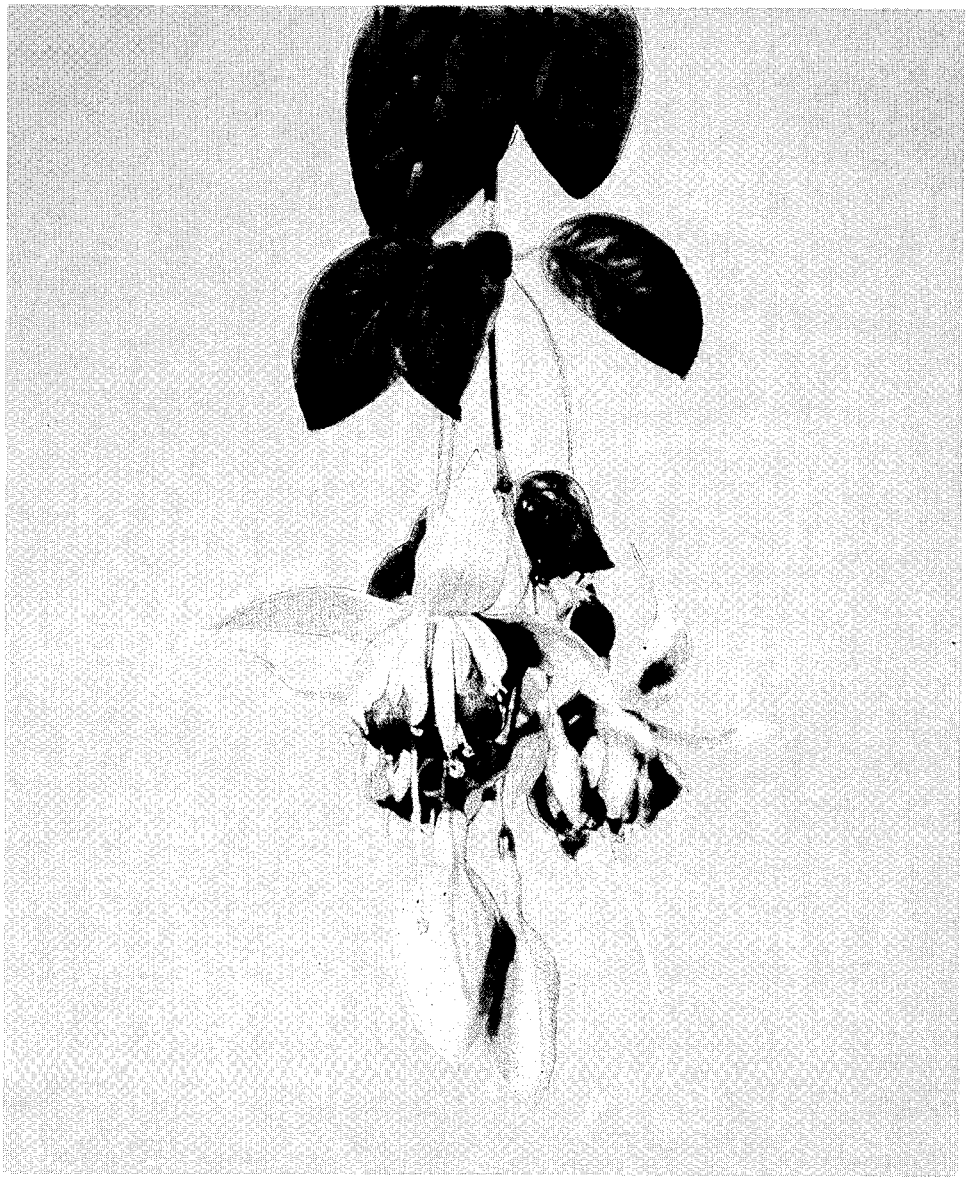
Horace M. Tiret
Inventor Patented July 28, 1953

Plant Pat. 1,206

UNITED STATES PATENT OFFICE 1,206

FUCHSIA PLANT

Horace M. Tiret, San Francisco, Calif.

Application October 25, 1949, Serial No. 123,497

1 Claim. (Cl. 47—60)

This invention relates to a new and improved fuchsia plant, and more particularly to a new and distinctive color distribution throughout the petals, whereby the many patterns of pink and purple on the outside petals produce a distinctive and striking bi-color effect.

This fuchsia plant was derived from many crossings, and is the immediate product of crossing two hybrid fuchsias, the Titanic (Victor Reiter, Jr.) (f.) and the Brazier (Victor Reiter, Jr.) (m.), neither patented. I employed the accepted principle of crossing two varieties of the Eufuchsia (m.) and the Quelusia (f.) groups. Experimental work and development was done at San Francisco, California.

In addition to the unusual color effect, the fuchsia is distinctive in form in that it is a double fuchsia, the extra petals of which are as long or nearly as long as the four center petals, giving a solid, closely knit, conformation, and the flower is larger and more double than other fuchsias of its class.

I have asexually reproduced this new variety at Palo Alto, Santa Clara County, Calif., where it has been asexually reproduced by cuttings, and its distinguishing characteristics have proved to be firmly fixed.

A detailed description of this new variety of fuchsia plant is as follows:

*Growth habits.*—This is an extremely vigorous plant, the branches of which are inclined to be rather firm, and naturally arching. In cooler climate it has a tendency toward softer, more bending growth. Blooms from approximately May through November.

*Foliage.*—The leaves are medium size, of a leathery texture with pronounced leaf veining and serrated edge.

*Bud.*—Medium in length, broadly "acorn" shaped, being broad at the base and tapering off to a point at the tip. Pink in color, with deeper pink overtones in tube and base of sepals.

*Flower.*—Medium large double corolla. The main petals are Rhodamine Purple (Horticultural Color Chart #29/1) fading to Rhodamine Purple (Horticultural Color Chart #29/2) at the base of the petal. The smaller outside petals are Rose Bengal (Horticultural Color Chart #25/2) or heavily marbled with that color. Sepals are long, broad, reflex type, colored inside Tynian Rose (Horticultural Color Chart #25/3), and colored outside at base Geranium Lake (Horticultural Color Chart #20/2), fading to creamy white at tip. The tube fades from Geranium Lake (Horticultural Color Chart #20/2) to shades of white. The flower is not fragrant.

*Ovary.*—Large and round, deep green in color.

*Petals (corolla).*—Medium large, double. There are four center petals which are slightly longer than the many outside petals which surround them. The petals are distinctively colored as described above.

*Stigma.*—White.

*Style.*—Pink.

*Stamens.*—Eight (pink).

*Anthers.*—White.

*Parentage.*—The parentage of this fuchsia is Titanic (Victor Reiter, Jr.) (f.) and Brazier (Victor Reiter, Jr.) (m.).

Having thus disclosed my discovery, I claim:

The new and distinct variety of double fuchsia plant substantially as described and illustrated characterized by its large double flower which is distinctive in form and whose petals are unusually bi-colored and having a solid closely-knit conformation.

HORACE M. TIRET.

References Cited in the file of this patent

UNITED STATES PATENTS

| Number | Name | Date |
|---|---|---|
| Pl. Pt. 610 | Hazard et al. | Dec. 7, 1943 |
| Pl. Pt. 925 | Reiter | Feb. 28, 1940 |